(12) United States Patent
Shimada et al.

(10) Patent No.: US 6,410,605 B1
(45) Date of Patent: Jun. 25, 2002

(54) PROCESS FOR PREPARING EMULSION

(75) Inventors: Toshiya Shimada; Kouichi Funada; Hidetake Nakamura; Hideaki Kubo, all of Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/531,482

(22) Filed: Mar. 20, 2000

(30) Foreign Application Priority Data

Mar. 19, 1999 (JP) ............................................. 11-076602

(51) Int. Cl.$^7$ ............................... B01F 3/12; C08F 2/32; C08K 9/04; C08K 9/10
(52) U.S. Cl. ..................... 516/22; 424/401; 427/213.34; 516/76; 516/928; 523/210; 524/801; 526/911
(58) Field of Search ............................ 516/22, 76, 928; 526/911; 427/213.34; 523/210; 524/801; 424/401

(56) References Cited

U.S. PATENT DOCUMENTS

| | | | | |
|---|---|---|---|---|
| 2,606,174 A | * | 8/1952 | Kolthoff et al. | ......... 526/911 X |
| 3,284,393 A | * | 11/1966 | Vanderhoff et al. | .......... 524/801 |
| 3,429,827 A | * | 2/1969 | Ruus | ......................... 264/4 X |
| 4,328,149 A | * | 5/1982 | Morse et al. | ........... 524/801 X |
| 4,608,401 A | | 8/1986 | Martin | ........................ 523/205 |
| 4,680,200 A | * | 7/1987 | Solc | ........................ 526/911 X |
| 4,832,858 A | * | 5/1989 | Vishnupad et al. | ..... 516/928 X |
| 5,015,469 A | * | 5/1991 | Yoneyama et al. | ........ 516/22 X |
| 5,133,992 A | * | 7/1992 | Nair et al. | ............... 526/911 X |
| 5,225,279 A | * | 7/1993 | Redlich et al. | ...... 427/213.34 X |
| 5,438,041 A | * | 8/1995 | Zheng et al. | ............. 516/76 X |

FOREIGN PATENT DOCUMENTS

| | | |
|---|---|---|
| EP | 0 882 498 | 12/1998 |
| FR | 1.543.806 | 9/1968 |
| FR | 2 258 165 | 8/1975 |
| GB | 1117224 | 6/1968 |
| GB | 2 002 652 | 2/1979 |
| JP | 62-234541 | 10/1987 |
| WO | WO 98/26752 | 6/1998 |

* cited by examiner

*Primary Examiner*—Richard D. Lovering
(74) *Attorney, Agent, or Firm*—Oblon, Spivak, McClelland, Maier & Neustadt, P.C.

(57) ABSTRACT

A process for preparing a solid particles-containing emulsion comprising mixing an oil droplets-in-water emulsion with lipophilic solid particles or a dispersion thereof, thereby allowing to include the lipophilic solid particles in the oil droplets. The solid particles-containing emulsion can be suitably used in paints, inks for ink jet printers, fiber-treated agents, coating materials, adhesives, skin cosmetics, hair cosmetics, and the like.

28 Claims, No Drawings

PROCESS FOR PREPARING EMULSION

BACKGROUND OF THE INVENTION

1. Field of the Invention

The present invention relates to a process for preparing an emulsion. More specifically, the present invention relates to a solid particles-containing emulsion which can be suitably used in paints, inks for ink jet printers, fiber-treated agents, coating-materials, adhesives, skin cosmetics, hair cosmetics, and the like.

2. Discussion of the Related Art

As a process for preparing an oil-in-water emulsion in which solid substances useful for liquid droplets are contained, there has been known a process comprising previously adding lipophilic solid particles to be contained to an oil, and thereafter emulsifying and dispersing the resulting mixture (Japanese Patent Laid-Open No. Sho 62-234541). However, in this process, since the viscosity becomes high when the content of the solid substances becomes high, there arise defects that the dispersion of the solid substance is likely to be difficult, and even when the solid substance is emulsified in a solvent incompatible with a solid-liquid mixture, its dispersion is likely to be difficult, so that the ratio of the solid substance cannot be increased.

In addition, when an emulsion prepared by emulsifying and dispersing oil droplets as polymerizable monomers is subjected to suspension polymerization, it is necessary to dissolve a polymerization initiator in a dispersed phase. However, a long period of time is required for dissolving the polymerization initiator in the solid-liquid mixture, and it is difficult to confirm that the polymerization initiator is dissolved. Therefore, there arises a defect that the dispersion of the solid substance is insufficient, because not so much time can be spent for the dispersion of the solid substance in the solution prepared by dissolving the polymerization initiator from the aspect of stability of the polymerization initiator.

An object of the present invention is to provide a process for preparing an emulsion which allows to include solid particles in oil droplets or water droplets (hereinafter simply referred to as "dispersion droplets"); and a process for preparing a solid particles-containing polymer emulsion comprising including a polymerizable monomer in the dispersion droplets of the emulsion, and polymerizing the polymerizable monomer.

Another object of the present invention is to provide a process for preparing an emulsion which allows to include solid particles in the dispersion droplets, wherein the dispersion droplets have a small average particle diameter and are substantially free from agglomerates.

SUMMARY OF THE INVENTION

According to the present invention, there are provided:

[1] a process for preparing a solid particles-containing emulsion comprising mixing an oil droplets-in-water emulsion with lipophilic solid particles or a dispersion thereof, thereby allowing to include the lipophilic solid particles in the oil droplets;

[2] a process for preparing a solid particles-containing emulsion comprising mixing a water droplets-in-oil emulsion with hydrophilic solid particles or a dispersion thereof, thereby allowing to include the hydrophilic solid particles in the water droplets; and

[3] a process for preparing a solid particles-containing polymer emulsion comprising including a polymerizable monomer in the water droplets, preparing solid particles-containing emulsion by the process according to item [1] or [2], and polymerizing the polymerizable monomer.

DETAILED DESCRIPTION OF THE INVENTION

The term "contain" as referred in the present invention encompasses not only the state in which the solid particles are incorporated in the dispersion droplets, but also the state in which a part of the solid particles is contained in the dispersion droplets or the state in which the solid particles are deposited on the surface of the dispersion droplets. In addition, the technical idea of the term "contain" also encompasses the state in which the dispersion droplets are polymer droplets, and the solid particles are deposited to the surface of polymer particles. The solid particles to be contained may be either an inorganic compound or an organic compound.

The term "lipophilic solid particles" as referred in the present specification means particles having a surface which forms a contact angle when brought into contact with water. The lipophilic solid particles include those having both lipophilic surface and hydrophilic surface and those in which a hydrophilic surface is surface-treated to give a hydrophilic surface having a lipophilic surface.

The lipophilic solid particles include organic pigments such as monoazo, dis-azo, benzimidazolone, quinacridone, phthalocyanine and other organic pigments; and inorganic pigments such as carbon black. It is desired that the lipophilic solid particles have an average particle diameter of preferably 0.05 to 10 $\mu$m, more preferably 0.05 to 5 $\mu$m, still more preferably 0.05 to 1 $\mu$m, from the viewpoint of the stability of the emulsion.

The term "hydrophilic solid particles" as referred in the present specification means particles having a surface which does not form a contact angle when brought into contact with water. The hydrophilic solid particles include those having both hydrophilic surface and lipophilic surface and those in which a lipophilic surface is surface-treated to give a lipophilic surface having a hydrophilic surface.

The hydrophilic solid particles include titanium oxide, silica, zeolite, barium sulfate, calcium carbonate, kaolin, iron oxides, and the like. It is desired that the hydrophilic solid particles have an average particle diameter of preferably 0.05 to 10 $\mu$m, more preferably 0.05 to 5 $\mu$m, still more preferably 0.05 to 1 $\mu$m, from the viewpoint of the stability of the emulsion.

When the solid particles are used in a form of dispersion, a dispersing agent for dispersing the solid particles is used as occasion demands.

The dispersing agent includes anionic surfactants such as dodecylsulfates, dodecylbenzenesulfonates, and sulfates of polyoxyethylene nonyl phenyl ethers; nonionic surfactants such as polyoxyethylene alkyl ethers, polyoxyethylene alkyl phenyl ethers, polyoxyethylene-polyoxypropylene block copolymers, and sucrose ester of fatty acids; cationic surfactants such as octadecyltrimethylammonium chloride; amphoteric surfactants such as alkyl dimethylaminoacetate betaines and 2-alkyl-N-carboxy-N-hydroxyimidazolium betaines; natural or synthetic high-molecular compounds such as polyvinyl alcohols, gelatin, polyvinyl pyrrolidones, polymethyl vinyl ethers, polybutadienes, proteins, hydroxyalkyl celluloses, polyurethane resins, and acrylic resins, and the like.

The component in the oil phase and the component in the water phase used during the preparation of an O/W or W/O emulsion are selected so that these components are incompatible with each other.

The component in the oil phase incompatible with water is preferably an organic compound having a solubility to water of not more than 1 g per 100 g of water at 20° C. The organic compound includes cyclohexane, n-hexane, benzene, cottonseed oil, rapeseed oil, squalane, squalene, waxes, styrene, divinylbenzene, butyl acrylate, 2-ethylhexyl acrylate, cyclohexyl acrylate, decyl acrylate, lauryl acrylate, dodecenyl acrylate, myristyl acrylate, palmityl acrylate, hexadecenyl acrylate, stearyl acrylate, octadecenyl acrylate, behenyl acrylate, butyl methacrylate, 2-ethylhexyl methacrylate, cyclohexyl methacrylate, decyl methacrylate, lauryl methacrylate, dodecenyl methacrylate, myristyl methacrylate, palmityl methacrylate, hexadecenyl methacrylate, stearyl methacrylate, octadecenyl methacrylate, behenyl methacrylate, silicone macromonomers, and the like.

The component in the water phase incompatible with the component in the oil phase includes water alone, and water solutions prepared by dissolving optional necessary ingredients in water.

When an emulsion is prepared, there can be used a dispersing agent such as the surfactants and the natural and/or synthetic high-molecular compounds listed above as occasion demands.

When allowing to include solid particles in oil droplets of an O/W emulsion, lipophilic solid particles are used. Alternatively, there can be used lipophilic solid particles prepared by treating the surface of hydrophilic solid particles with a surface modifier to impart lipophilicity to the surface.

On the other hand, when allowing to include the solid particles in the water droplets of a W/O emulsion, hydrophilic solid particles are used. Alternatively, there can be used hydrophilic solid particles prepared by treating the surface of lipophilic solid particles with a surface modifier to impart hydrophilicity to the surface.

It is preferable that the lipophilic solid particles have substantially non-polar surfaces, and show little interactions with water molecules (easily to be wetted with water).

In addition, it is preferable that the hydrophilic solid particles have a largely polar surface, and show large interactions with water molecules (easily wetted with water).

The surface modifier includes anionic surfactants such as dodecylsulfates, dodecylbenzenesulfonates, and sulfates of polyoxyethylene nonyl phenyl ethers; nonionic surfactants such as polyoxyethylene alkyl ethers, polyoxyethylene alkyl phenyl ethers, and polyglycerol fatty acid esters; cationic surfactants such as octadecyltrimethylammonium chloride; amphoteric surfactants such as alkyl dimethylaminoacetate betaines, 2-alkyl-N-carboxy-N-hydroxyimidazolium betaines and lecithin; coupling agents such as phosphate coupling agents, silane coupling agents, and titanate coupling agents; high molecular-coating surface modifiers such as polydimethyl siloxanes, and the like. These surface modifiers can be used for either of a case where the surface of the lipophilic solid particles is modified to have hydrophobicity or a case where the surface of the hydrophilic solid particles is modified to have lipophilicity.

First, a process for preparing a solid particles-containing emulsion comprising preparing an O/W emulsion, and mixing the resulting emulsion with lipophilic solid particles or a dispersion thereof, thereby allowing to include the lipophilic solid particles in the oil droplet will be explained.

An O/W emulsion is prepared by mixing a component in the water phase prepared by dissolving a dispersing agent in water with a hardly water-soluble component in the oil phase, and emulsifying the mixture. As the means for emulsification, there can be preferably employed shearing machines, including high-speed shearing emulsifiers such as homomixers, ultratalacs and milders, and high-pressure homogenizers; ultrasonic wave emulsifiers, and the like. The ratio of the component in the oil phase to the component in the water phase may be a given value, and it is preferable that the ratio of the oil phase is 0.5 to 50% by weight, from the viewpoint of operability. It is preferable that the dispersion droplets of the emulsion have an average particle diameter of 0.1 to 30 μm. The average particle diameter is more preferably 0.1 to 10 μm, from the viewpoint of narrowing the particle diameter distribution of the dispersion droplets of the solid particles-containing emulsion after allowing to include the lipophilic solid particles in the component in the oil phase. The average particle diameter of the dispersion droplets of the emulsion can be determined by using a laser scattering particle diameter analyzer "LA-910" commercially available from Horiba, LTD.

The O/W emulsion obtained in the manner described above is mixed with lipophilic solid particles or a dispersion thereof. The lipophilic solid particles may be either organic particles or inorganic particles. An embodiment of addition of the particles is not limited to specified ones. When the diameter of the particles is small, it is desired to use the lipophilic solid particles in the form of a water dispersion prepared by dispersing the lipophilic solid particles in a component in the water phase, because it would be difficult to homogeneously disperse the lipophilic solid particles when added in the form of powder. A process for dispersing the lipophilic solid particles in the component in the water phase may be a known process, and a dispersing agent can be used during dispersion as occasion demands.

The solid particles-containing emulsion can be obtained by mixing an O/W emulsion with the lipophilic solid particles or a dispersion thereof to migrate the lipophilic solid particles existing in the component in the water phase to the component in the oil phase, thereby allowing to include the lipophilic solid particles in the oil droplets.

The amount of the lipophilic solid particles contained in the oil phase is preferably 0.5 to 80 parts by weight, and more preferably 1 to 50 parts by weight, based on 100 parts by weight of the component in the oil phase, from the viewpoint of the stability of the emulsion.

The means for allowing to include the lipophilic solid particles in the component in the oil phase may be simply bombardment of the solid particles with the oil droplets by means of agitation, or the like. From the viewpoint of more rapidly and securely allowing to include the lipophilic solid particles in the component in the oil phase, it is preferable to apply a shear to the oil droplets to finely divide the oil droplets, thereby making it possible to increase a contact frequency of the oil droplets and the solid particles. In addition, when the oil droplets are finely divided, their surface areas are increased, so that the amount of the dispersing agent relative to the finely divided particles is deficient, thereby having an unstable state. However, since the finely divided liquid droplets are unified into one body, the unified droplet becomes a stable state, and the solid particles are incorporated into the oil droplets during the unification.

The means for applying a shear include high-speed shearing emulsifiers such as homomixers, milders and colloidal mills, and high-pressure homogenizers; and the means for applying ultrasonic waves include ultrasonic wave emulsifiers, without being limited thereto as long as a shearing force or ultrasonic waves are applied to the mixture. Among them, it is preferable to use high-speed shearing emulsifiers such as homomixers, milders, colloidal mills, and ultratalacs, filmics, or high-pressure homogenizers, from the viewpoint of productivity. It is preferable that the shearing force is not less than 50 Pa in order to adjust the content of the solid particles to a practically desirable level of not less than 40% by weight. It is desired that the shearing force is not less than 100 Pa, from the viewpoint of more rapidly including the solid particles.

In the present invention, the shearing force is expressed by the equation (I):

$$\tau = \mu \cdot S \qquad (I)$$

wherein $\mu$ is viscosity (Pa·s) of a fluid; and S is a shear rate expressed by the equation (II):

$$S = du/dy \qquad (II)$$

wherein u is a linear velocity (m/s) [when a high-speed shearing emulsifier is used, the linear velocity corresponds to a tip speed of a rotatable part; and when a high-pressure homogenizer is used, the linear velocity corresponds to a velocity of the fluid flowing through the homogenizing valve; and when a mixing vessel is used, the linear velocity corresponds to a peripheral speed of a tip end of agitation impellers]; and y is a distance (m) in a direction perpendicular to a migrating surface [when a high-speed shearing emulsifier is used, the distance corresponds to a distance from a tip end of a rotor to a stator; when a high-pressure homogenizer is used, the distance corresponds to a gap between the homovalves through which the fluid passes; and when a mixing vessel is used, the distance corresponds to a distance from a tip end of agitation impellers to a vessel wall].

It is preferable that the shearing rate is not less than $50 \times 10^3$ s$^{-1}$, in order to more efficiently adjust the content of the solid particles to not less than 40% by weight, and it is more preferable that the shearing rate is not less than $100 \times 10^3$ s$^{-1}$, from the viewpoint of rapidly allowing to include the solid particles in the droplets. In addition, it is preferable that the shearing rate is not more than $150 \times 10^3$ s$^{-1}$, from the viewpoint of adjusting the content of the solid particles to not less than 50% by weight, and it is preferable that the shearing rate is not more than $100 \times 10^9$ s$^{-1}$, from the viewpoint of avoiding the destruction of the solid particles or agglomeration of the solid particles. Incidentally, when the ultrasonic waves are utilized, it is desired that shearing is carried out at an output of not less than 3 kW/m$^2$.

Next, a process for preparing a solid particles-containing emulsion comprising mixing the W/O emulsion with hydrophilic solid particles or a dispersion thereof, thereby including the hydrophilic solid particles in the water droplets will be explained.

A W/O emulsion is prepared by mixing a hardly water-soluble component in the oil phase in which the dispersing agent is dissolved with water or a component in the water phase prepared by dissolving a water-soluble component in water, and emulsifying the mixture. The emulsification process may be the same as the process when the O/W emulsion is prepared. The ratio of the component in the water phase to the component in the oil phase may be optionally selected, and it is preferable that the ratio of the water phase is 0.5 to 50% by weight, from the viewpoint of operability. The dispersion droplets of the emulsion have an average particle diameter of preferably 0.1 to 30 μm, and more preferably 0.1 to 10 μm from the viewpoint of narrowing the particle diameter distribution of the dispersion droplets of the solid particles-containing emulsion after allowing to include the hydrophilic solid particles in the component in the water phase. The average particle diameter of the dispersion droplets can be determined in accordance with the same method as above.

The W/O emulsion obtained in the manner described above is mixed with hydrophilic solid particles or a dispersion thereof. The hydrophilic solid particles may be either organic particles or inorganic particles. An embodiment of addition of the particles is not limited to specified ones. When the diameter of the particles is small, it is desired to use the hydrophilic solid particles in the form of an oil dispersion prepared by dispersing the hydrophilic solid particles in a component in the water phase, because it would be difficult to homogeneously disperse the hydrophilic solid particles when added in the form of powder. A process for dispersing the hydrophilic solid particles in the component in the oil phase may be a known process, and a dispersing agent can be used during dispersion as occasion demands.

The solid particles-containing emulsion can be obtained by mixing a W/O emulsion with the hydrophilic solid particles or a dispersion thereof to migrate the hydrophilic solid particles existing in the component in the oil phase to the component ir the water phase, thereby allowing to include the hydrophilic solid particles in the water droplets.

The amount of the hydrophilic solid particles contained in the component in the water phase and the means for applying a shearing force or ultrasonic waves when the average particle diameter of the dispersion droplets is not less than 1 μm may be the same as those of the preparation of the solid particles-containing emulsion using the W/O emulsion.

In addition, when an O/W emulsion is used, the solid particles-containing polymer emulsion can be obtained by including the lipophilic solid particles in oil droplets comprising lipophilic polymerizable monomers and an oil-soluble polymerization initiator, and polymerizing the polymerizable monomers. On the other hand, when a W/O emulsion is used, the solid particles-containing polymer emulsion can be obtained by including the hydrophilic solid particles in water droplets comprising hydrophilic polymerizable monomers or a mixture comprising water and hydrophilic polymerizable monomers, and a water-soluble polymerization initiator, and polymerizing the polymerizable monomers.

When either an O/W emulsion or a W/O emulsion is used, the core-shell type solid particles-containing polymer emulsion can be obtained by including the polymerizable monomers in the continuous phase, and polymerizing the polymerizable monomers in the dispersed phase and concurrently polymerizing the polymerizable monomers in the continuous phase.

The lipophilic polymerizable monomers are preferably those having a solubility to water of not more than 1 g per 100 g of water at 20° C. The lipophilic polymerizable monomers includes, for instance, styrene, divinylbenzene, butyl acrylate, 2-ethylhexyl acrylate, cyclohexyl acrylate, decyl acrylate, lauryl acrylate, dodecenyl acrylate, myristyl acrylate, palmityl acrylate, hexadecenyl acrylate, stearyl acrylate, octadecenyl acrylate, behenyl acrylate, butyl methacrylate, 2-ethylhexyl methacrylate, cyclohexyl methacrylate, decyl methacrylate, lauryl methacrylate, dodecenyl methacrylate, myristyl methacrylate, palmityl methacrylate, hexadecenyl methacrylate, stearyl methacrylate, octadecenyl methacrylate, behenyl methacrylate, silicone macromonomers, and the like. These lipophilic polymerizable monomers may be used alone or in admixture of two or more kinds.

The hydrophilic polymerizable monomers include unsaturated carboxylic acid monomers such as acrylic acid, methacrylic acid, itaconic acid and maleic acid; unsaturated sulfonic acid monomers such as styrenesulfonic acid, 2-acrylamide-2-methylpropane sulfonic acid, 3-sulfopropylacrylate, 3-sulfopropylmethacrylate, and vinylsulfonic acid; unsaturated phosphate monomers, such as vinyl phosphate, diphenyl-2-acryloyloxyethyl phosphate and diphenyl-2-methacryloyloxyethyl phosphate; N,N-dimethylacrylamide, and the like. These hydrophilic polymerizable monomers can be used alone or in admixture of two or more kinds.

As the oil-soluble polymerization initiator, there can be generally used those which initiate addition polymerization of the monomers by radical decomposition with heating or in the presence of a reducible substance. The oil-soluble polymerization initiator includes, for instance, organic peroxides such as lauroyl peroxide and benzoyl peroxide; and azo compounds such as 2,2'-azobisisobutyronitrile, 2,2'-azobis(2,4-dimethylvaleronitrile) and 2,2'-azobis(2-methylbutyronitrile). These polymerization initiators may be used alone or in admixture of two or more kinds.

The water-soluble polymerization initiators are those which initiate addition polymerization of the monomers by radical decomposition with heating or in the presence of a reducible substance. There can be generally used water-soluble peroxodisulfates, peroxides, azobis compounds, and the like. The water-soluble polymerization initiator includes, for instance, peroxodisulfates such as potassium persulfate and ammonium persulfate; peroxides such as hydrogen peroxide and t-butyl hydroperoxide; and azo compounds such as 2,2'-azobis-2-amidinopropane salt and 4,4'-azobis-4-cyanopentanoic acid. The water-soluble polymerization initiator can also be used as a redox initiator by using together with a reducing agent.

The solid particles-containing polymer emulsion obtained by the present invention can be suitably used for, for instance, paints, inks for ink jet printers, fiber-treated agents, coating materials, adhesives, skin cosmetics, hair cosmetics, and the like. Specifically, the solid particles-containing polymer emulsion is suitable for skin cosmetics, hair cosmetics, and the like.

EXAMPLES

Example 1

The amount 40 g of a blue pigment (commercially available from DAINICHISEIKA COLOR & CHEMICALS MFG. CO., LTD. under the trade name of "Pigment Blue-15"), 10 g of a nonionic surfactant (commercially available from Kao Corporation under the trade name of "EMULGEN 2025G") and 150 g of ion-exchanged water were mixed, and the resulting mixture was dispersed with a beads-mill (commercially available from MITSUI MINING COMPANY LTD. under the trade name of "Attritor MA-01SC") for 10 hours, to give of a pigment/water dispersion.

On the other hand, a one-liter glass beaker was charged with 25 g of stearyl methacrylate and 0.3 g of lauroyl peroxide, and the ingredients were dissolved. Five-hundred grams of ion-exchanged water and 5 g of a nonionic surfactant (commercially available from Kao Corporation under the trade name of "EMULGEN 2025G") were added to the resulting solution, and the resulting mixture was emulsified with a homomixer (commercially available from Tokushu Kika Kogyo Kabushiki Kaisha under the model number of "HV-M"), to give an O/W emulsion comprising droplets having an average particle diameter of 1.24 $\mu$m.

The amount 530.5 g of this O/W emulsion was mixed with 44 g of the previously prepared pigment/water dispersion, and a shear was further applied to the resulting mixture at a shear rate of $900 \times 10^3$ $s^{-1}$ with the homomixer, to give a pigment-containing emulsion comprising droplets having an average particle diameter of 0.86 $\mu$m. The amount of the solid particles was 35 parts by weight, based on 100 parts by weight of the component in the oil phase.

The pigment-containing emulsion was transferred to a one-liter glass reaction vessel, and the atmosphere of the reaction vessel was replaced with nitrogen gas. Thereafter, the ingredients were heated to an internal temperature of 75° C. with stirring. The polymerization was carried out for 3 hours with stirring, to give a pigment-containing polymer emulsion.

Example 2

The amount 40 g of a blue pigment (commercially available from DAINICHISEIKA COLOR & CHEMICALS MFG. CO., LTD. under the trade name of "Pigment Blue-15"), 16 g of a nonionic surfactant (commercially available from Kao Corporation under the trade name of "EMULGEN 2025G") and 144 g of ion-exchanged water were mixed, and the mixture was dispersed with a beads-mill (commercially available from MITSUI MINING COMPANY LTD. under the trade name of "Attritor MA-01SC") for 10 hours, to give of a pigment/water dispersion.

On the other hand, a one-liter glass beaker was charged with 25 g of stearyl methacrylate and 0.3 g of lauroyl peroxide, and the ingredients were dissolved. Five-hundred grams of ion-exchanged water and 5 g of a nonionic surfactant (commercially available from Kao Corporation under the trade name of "EMULGEN 2025G") were added to the resulting solution, and the resulting mixture was emulsified with a high-pressure homogenizer (commercially available from Rannie under the model number of "GM-1"), to give an O/W emulsion comprising droplets having an average particle diameter of 0.16 $\mu$m.

The amount 530.5 g of the resulting O/W emulsion was mixed with 44 g of the previously prepared pigment/water dispersion, to give a pigment-containing emulsion comprising droplets having an average particle diameter of 0.36 $\mu$m. The amount of the solid particles was 35 parts by weight, based on 100 parts by weight of the component in the oil phase.

The resulting pigment-containing emulsion was transferred to a one-liter glass reaction vessel, and the atmosphere of the reaction vessel was replaced with nitrogen gas. Thereafter, the ingredients were heated to an internal temperature of 75° C. with stirring. The polymerization was carried out for 3 hours with stirring, to give a pigment-containing polymer emulsion.

Example 3

The amount 40 g of a black pigment (commercially available from Mikuni Shikiso Kabushiki Kaisha, titanium black), 15 g of a nonionic surfactant (commercially available from Mitsubishi Chemical Foods Company, Ltd. under the trade name of "fatty acid sucrose ester S-770"), and 150 g of cyclohexane were mixed together. Thereafter, the resulting mixture was dispersed in the same beads-mill as that used in Example 1 for 10 hours, to give a pigment/oil dispersion.

Next, 190 g of cyclohexane and 0.6 g of a nonionic surfactant (commercially available from Mitsubishi Chemical Foods Company, Ltd. under the trade name of "fatty acid sucrose ester S-770") were mixed in a one-liter glass beaker, and the ingredients were dissolved, to give a surfactant cyclohexane solution.

Subsequently, a 0.5-liter glass beaker was charged 77 g of ion-exchanged water, 29 g of a 90% aqueous methacryloyloxyethylene diethyl sulfate solution, 31 g of N,N-dimethylacrylamide and 0.15 g of potassium peroxodisulfate, and the mixture was homogeneously mixed. Thereafter, the homogeneous mixture was added to the previously prepared cyclohexane solution of the surfactant, and the resulting mixture was emulsified with a homomixer, to give a W/O emulsion comprising droplets having an average particle diameter of 3.12 $\mu$m.

This W/O emulsion and 31 g of the previously prepared pigment/oil dispersion were mixed together, and a shear was further applied to the mixture at a shear rate of $40 \times 10^3$ $s^{-1}$ with a homomixer, to give a pigment-containing emulsion comprising droplets having an average particle diameter of 2.66 $\mu$m. The amount of the solid particles was 7.6 parts by weight, based on 100 parts by weight of the component in the water phase. This pigment-containing emulsion was transferred to a one-liter glass reaction vessel, and the atmosphere of the reaction vessel was replaced with nitrogen gas. Thereafter, the ingredients were heated to an internal temperature of 68.5° C. with stirring. The polymerization was carried out for 3 hours with stirring, to give a pigment-containing polymer emulsion.

Example 4

The same procedures as in Example 2 were carried out, except that mixing was carried out with applying a shear to the mixture at a shear rate of $30 \times 10^3$ $s^{-1}$ with a homomixer during mixing the emulsion and the pigment, to give a pigment-containing emulsion having an average particle diameter of 0.49 $\mu$m. This pigment-containing emulsion was transferred to a one-liter glass reaction vessel, and the atmosphere of the reaction vessel was replaced with nitrogen gas. Thereafter, the ingredients were heated to an internal temperature of 75° C. with stirring. The polymerization was carried out for 3 hours with stirring, to give a pigment-containing polymer emulsion.

Example 5

The amount 40 g of a blue pigment (commercially available from DAINICHISEIKA COLOR & CHEMICALS MFG. CO., LTD. under the trade name of "Pigment Blue-15"), 10 g of a nonionic surfactant (commercially available from Kao Corporation under the trade name of "EMULGEN 2025G") and 150 g of ion-exchanged water were mixed, and the mixture was dispersed with the same beads-mill used in Example 1 for 10 hours, to give of a pigment/water dispersion.

On the other hand, a one-liter glass beaker was charged with 25 g of stearyl methacrylate and 0.3 g of lauroyl peroxide, and the ingredients were dissolved. To the resulting solution were added 500 g of ion-exchanged water and 0.01 g of a nonionic surfactant (commercially available from Kao Corporation under the trade name of "EMULGEN 2025G"), and the resulting mixture was emulsified with the same high-pressure homogenizer used in Example 2, to give an O/W emulsion comprising droplets having an average particle diameter of 5.90 $\mu$m.

The amount 530.5 g of the resulting O/W emulsion was mixed with 44 g of the previously prepared pigment/water dispersion, and a shear was applied to the mixture at a shear rate of $100 \times 10^3$ $s^{-1}$ with a homomixer during mixing, to give a pigment-containing emulsion comprising droplets having an average particle diameter of 0.95 $\mu$m. The amount of the solid particles was 35 parts by weight, based on 100 parts by weight of the component in the oil phase.

The resulting pigment-containing emulsion was transferred to a one-liter glass reaction vessel, and the atmosphere of the reaction vessel was replaced with nitrogen gas. Thereafter, the ingredients were heated to an internal temperature of 75° C. with stirring. The polymerization was carried out for 3 hours with stirring, to give a pigment-containing polymer emulsion.

Example 6

The same procedures as in Example 5 were carried out, except that mixing was carried out with applying a strong shear at a shear rate of $2500 \times 10^3$ $s^{-1}$ with the same high-pressure homogenizer as in Example 2 to the mixture during mixing of the O/W emulsion with the pigment/water dispersion, to give a pigment-containing emulsion having an average particle diameter of 0.86 $\mu$m. The amount of the solid particles was 35 parts by weight, based on 100 parts by weight of the component in the oil phase.

This pigment-containing emulsion was transferred to a one-liter glass reaction vessel, and the atmosphere of the reaction vessel was replaced with nitrogen gas. Thereafter, the ingredients were heated to an internal temperature of 75° C. with stirring. The polymerization was carried out for 3 hours with stirring, to give a pigment-containing polymer emulsion.

Example 7

The same procedures as in Example 5 were carried out, except that mixing was carried out with applying a strong shear at an output of 400 kW/m$^2$ to the mixture during mixing of the O/W emulsion and the pigment/water dispersion with an ultrasonic emulsifier (commercially available from Nippon Seiki K. K. under product number of "US-600T"), to give a pigment-containing emulsion having an average particle diameter of 0.68 $\mu$m. The amount of the solid particles was 35 parts by weight, based on 100 parts by weight of the component in the oil phase.

This pigment-containing emulsion was transferred to a one-liter glass reaction vessel, and the atmosphere of the reaction vessel was replaced with nitrogen gas. Thereafter, the ingredients were heated to an internal temperature of 75° C. with stirring. The polymerization was carried out for 3 hours with stirring, to give a pigment-containing polymer emulsion.

Example 8

The same procedures as in Example 7 were carried out, except that mixing was carried out with applying a weak shear at an output of 1 kW/m$^2$ to the mixture during mixing of the O/W emulsion with the pigment/water dispersion with the same ultrasonic emulsifier as in Example 7, to give a pigment-containing emulsion having an average particle diameter of 10.26 $\mu$m. The amount of the solid particles was 35 parts by weight, based on 100 parts by weight of the component in the oil phase.

This pigment-containing emulsion was transferred to a one-liter glass reaction vessel, and the atmosphere of the reaction vessel was replaced with nitrogen gas. Thereafter, the ingredients were heated to an internal temperature of 75°

C. with stirring. The polymerization was carried out for 3 hours with stirring, to give a pigment-containing polymer emulsion.

Example 9

A one-liter glass beaker was charged with 50 g of stearyl methacrylate and 0.5 g of lauroyl peroxide, and the ingredients were dissolved. Five-hundred grams of ion-exchanged water and 5 g of a nonionic surfactant (commercially available from Kao Corporation under the trade name of "EMULGEN 2025G") were added to the resulting solution, and the resulting mixture was emulsified with a homomixer (commercially available from Tokushu Kika Kogyo Kabushiki Kaisha under the model number of "HV-M"), to give an O/W emulsion comprising droplets having an average particle diameter of 1.35 µm.

The resulting O/W emulsion was transferred to a one-liter glass reaction vessel, and the atmosphere of the reaction vessel was replaced with nitrogen gas. Thereafter, the ingredients were heated to an internal temperature of 75° C. with stirring. The polymerization was carried out for 3 hours with stirring, to give a polymer emulsion. A one-liter glass beaker was charged with an entire amount of the resulting polymer emulsion and 10 g of pigment/water dispersion prepared in the same manner as in Example 1, and a shear was further applied to the mixture at a shear rate of $40 \times 10^3$ $s^{-1}$ with the homomixer, to give a pigment-containing polymer emulsion. The amount of the solid particles was 4 parts by weight, based on 100 parts by weight of the component in the oil phase.

Comparative Example 1

The amount 40 g of a blue pigment (commercially available from DAINICHISEIKA COLOR & CHEMICALS MFG. CO., LTD. under the trade name of "Pigment Blue-15"), 10 g of a nonionic surfactant (commercially available from Kao Corporation under the trade name of "EMULGEN 2025G") and 150 g of ion-exchanged water were mixed together, and the mixture was dispersed with the same beads-mill as that used in Example 1 for 10 hours, to give a pigment/water dispersion.

On the other hand, a one-liter glass beaker was charged with 50 g of stearyl methacrylate and 0.5 g of lauroyl peroxide, and the ingredients were dissolved, and 500 g of ion-exchanged water and 5 g of a nonionic surfactant (commercially available from Kao Corporation under the trade name of "EMULGEN 2025G") were added to the resulting mixture. Thereafter, 44 g of the previously prepared pigment/water dispersion was mixed therewith without emulsifying with a homomixer (commercially available from Tokushu Kika Kogyo Kabushiki Kaisha under the model number of "HV-M"), and a shear was further applied to the mixture at a shear rate of $40 \times 10^3$ $s^{-1}$ with a homomixer to mix the ingredients. The resulting mixture was transferred into a one-liter glass reaction vessel, and the atmosphere of the reaction vessel was replaced with nitrogen gas. Thereafter, the ingredients were heated to an internal temperature of 75° C. with stirring, and the polymerization was carried out with stirring for 3 hours. The resulting product contained a large number of coarse agglomerates having a diameter of not less than 100 µm, thereby providing a poor emulsion state.

Comparative Example 2

The amount 250 g of stearyl methacrylate, 100 g of a blue pigment ("Pigment Blue-15") and 25 g of a nonionic surfactant (commercially available from Kao Corporation under the trade name of "EMULGEN 2025G") were mixed together, and the mixture was dispersed with the same beads-mill used in Example 1 for 10 hours, to give a pigment/oil dispersion. The viscosity of the resulting pigment/oil dispersion was about 4500 mPa·s at 20° C. The amount 30.8 g of this pigment/oil dispersion was taken out therefrom, and 0.5 g of lauroyl peroxide was added thereto and dissolved. Thereafter, the mixture was added to an aqueous surfactant solution prepared by dissolving 7.2 g of EMULGEN 2025G in 500 g of ion-exchanged water, and the resulting mixture was emulsified with a homomixer. However, the viscosity of the pigment/oil dispersion was so high that the component in the oil phase could not be dispersed, and a suitable emulsion could not be prepared. The amount of the solid particles was 40 parts by weight, based on 100 parts by weight of the component in the oil phase.

With respect to each of the polymer emulsions prepared in Examples and Comparative Examples, a volume-average particle diameter, an amount of solid particles, an emulsion appearance, a surface appearance of polymer emulsion and a contact area of solid particles-emulsion were evaluated by the following methods. The results are shown in Table 1.

Evaluation Method (A) Average Particle Diameter

A volume-average particle diameter was measured by light scattering method using a particle diameter analyzer (commercially available by HORIBA, Ltd. under the model number of "LA-910").

(B) Content of Solid Particles

1) A 10 g dilute solution is prepared by diluting a pigment-containing emulsion with ion-exchanged water, to have a concentration of the solid particles of 0.02% by weight.

2) A 50 ml beaker is charged with the dilute solution and isopropyl palmitate (IPP) in an amount equal weight to the dilute solution. Here, the ingredients are gently added so that the IPP is not mixed with an aqueous phase.

3) The mixture is stirred for 5 minutes with a magnetic stirrer by setting a rotational speed to 600 rpm.

4) After the stirring is stopped, the mixture is allowed to stand for 5 minutes, to allow the separation of aqueous and oil phases.

5) Three grams of a sample is taken out from the IPP phase, which is an upper layer.

6) One gram of 2-benzyloxyethanol (BOE) is added thereto and dissolved, to give a solution.

7) The absorbance (at 518 nm) of the resulting solution is determined, and the content of free solid particles (% by weight) is calculated from the calibration curve of the absorbance and the content of the free solid particles.

8) The content of the solid particles other than the free solid particles is calculated as a content of the solid particles contained in the emulsion. The content of solid particles is calculated by the following equation.

[Content of Solid Particles] (% by weight)=100−[Content of Free Solid Particles]

(C) Emulsion Appearance

The emulsion after polymerization was observed by naked eyes.

(D) Surface Appearance of Polymer Particles

The surface of the polymer particles was observed by an optical microscope (magnification:×10000). Incidentally, in Table 1, the phrase "containing solid particles" refers to a state in which the solid particles are incorporated in the oil droplets and hardly existed on the oil droplet surface; the phrase "partially containing solid particles" refers to a state in which some of solid particles are incorporated in the oil droplets, some of solid particles are present outside of the oil droplets, and some of solid particles are partly contacted with the surface of the oil droplets; and the phrase "contacting with solid particles" refers to a state in which solid particles are hardly incorporated in the oil droplets and partly contacted with the surface of the oil droplets.

(E) Contact Area of Solid Particles-Emulsion

The emulsion was observed by an optical microscope (magnification:×10000), and the contact area was evaluated by the following criteria.

Evaluation Criteria

A: A state in which the polymer is almost completely covering the surface of the solid particles, and the contact area is almost equal to the surface area of the solid particles.

B: A state in which the polymer is covering a part of the solid particles.

C: A state in which most of the solid particles are existing outside of the polymer, a part of which is in contact with the polymer.

a high level of amounts of solid particles in the dispersed phase of the emulsion.

What is claimed is:

1. A process for preparing an emulsion containing lipophilic solid particles, comprising:

mixing a first oil-in-water emulsion with lipophilic solid particles or a dispersion of lipophilic solid particles to form a mixture, wherein said first emulsion comprises oil droplets; and applying a shear to the mixture with a shearing machine at a shearing rate of not less than $50 \times 10^3$ $s^{-1}$ to form a second oil-in-water emulsion containing lipophilic solid particles;

wherein the lipophilic solid particles are present in the second emulsion in an amount of not less than 40% by weight, based on the weight of the second emulsion; and wherein the oil droplets contain the lipophilic solid particles in the second emulsion.

2. The process according to claim 1, further comprising finely dividing the oil droplets prior to and/or during the shearing.

3. The process according to claim 1, wherein the oil droplets in the second oil-in-water emulsion are unified into

TABLE 1

| Example No. | Volume-Average Particle Size (μm) | Content of Solid Particles (% by wt.) | Emulsion Appearance | Surface Appearance of Polymer Particles | Contact Area of Solid Particles-Emulsion | Remarks |
|---|---|---|---|---|---|---|
| 1 | 0.86 | 70 | No Agglomerates | Containing Solid Particles | A | |
| 2 | 0.84 | 5 | Agglomerates Existed | Partially Containing Solid Particles | C | |
| 3 | 2.66 | 30 | Agglomerates Existed | Partially Containing Solid Particles | C | |
| 4 | 0.70 | 30 | Agglomerates Existed | Contacting with Solid Particles | C | |
| 5 | 0.82 | 40 | No Agglomerates | Partially Containing Solid Particles | B | |
| 6 | 0.76 | 70 | No Agglomerates | Containig Solid Particles | A | |
| 7 | 1.66 | 70 | No Agglomerates | Containig Solid Particles | A | |
| 8 | 10.26 | <10 | Agglomerates Existed | Contacting with Solid Particles | C | |
| 9 | 9.83 | 30 | No Agglomerates | Contacting with Solid Particles | C | |
| Comp. Example 1 | 234.2 | <10 | Much Agglomerates Existed | Contacting with Solid Particles | C | It does not appear to be emulsion. |
| Comp. Example 2 | — | 70< | No Emulsion Formed | Containing Solid Particles | A | Particle diameter is uneven, having poor stability. |

As is clear from the results shown in Table 1, according to each of Examples, there can be obtained emulsions having one body during and/or after the formation of the second oil-in-water emulsion.

4. The process according to claim 1, wherein said oil droplets comprise one or more polymerizable monomers; and wherein the process further comprises, after the formation of the second oil-in-water emulsion, polymerizing the polymerizable monomers.

5. The process according to claim 1, wherein the lipophilic solid particles are selected from the group consisting of organic and inorganic pigments.

6. The process according to claim 1, wherein the lipophilic solid particles are selected from the group consisting of monoazo organic pigment, dis-azo organic pigment, benzimidazolone organic pigment, quinacridone organic pigment, phthalocyanine organic pigment, and carbon black.

7. The process according to claim 1, wherein the lipophilic solid particles are comprised within the oil droplets.

8. The process according to claim 1, wherein the lipophilic solid particles are deposited on a surface of the oil droplets.

9. A process for preparing an emulsion containing lipophilic solid particles, comprising:

mixing a first oil-in-water emulsion with lipophilic solid particles of a dispersion of lipophilic solid particles to form a mixture, wherein said first emulsion comprises oil droplets; and sonicating the mixture with an ultrasonic dispersion device at an output of not less than 3 kW/m$^2$, to form a second oil-in-water emulsion containing lipophilic solid particles;

wherein the lipophilic solid particles are present in the second emulsion in an amount of not less than 40% by weight, based on the weight of the second emulsion; and wherein the oil droplets contain the lipophilic solid particles in the second emulsion.

10. The process according to claim 9, further comprising finely dividing the oil droplets prior to and/or during the sonicating.

11. The process according to claim 9, wherein the oil droplets in the second oil-in-water emulsion are unified into one body during and/or after the sonicating.

12. The process according to claim 9, wherein said oil droplets comprise one or more polymerizable monomers; and wherein the process further comprises, after the formation of the second oil-in-water emulsion, polymerizing the polymerizable monomers.

13. The process according to claim 9, wherein the lipophilic solid particles are selected from the group consisting of organic and inorganic pigments.

14. The process according to claim 9, wherein the lipophilic solid particles are selected from the group consisting of monoazo organic pigment, dis-azo organic pigment, benzimidazolone organic pigment, quinacridone organic pigment, phthalocyanine organic pigment, and carbon black.

15. The process according to claim 9, wherein the lipophilic solid particles are comprised within the oil droplets.

16. The process according to claim 9, wherein the lipophilic solid particles are deposited on a surface of the oil droplets.

17. A process for preparing an emulsion containing hydrophilic solid particles, comprising:

mixing a first water-in-oil emulsion with hydrophilic solid particles or a dispersion of hydrophilic solid particles to form a mixture, wherein said first emulsion comprises water droplets; and applying a shear to the mixture with a shearing machine at a shearing rate of not less than 50×10$^3$ s$^{-1}$ to form a second water-in-oil emulsion containing hydrophilic solid particles;

wherein the hydrophilic solid particles are present in the second emulsion in an amount of not less than 40% by weight, based on the weight of the second emulsion; and wherein the water droplets contain the hydrophilic solid particles in the second emulsion.

18. The process according to claim 17, further comprising finely dividing the water droplets prior to and/or during the shearing.

19. The process according to claim 17, wherein said water droplets comprise one or more polymerizable monomers; and wherein the process further comprises, after the formation of the second water-in-oil emulsion, polymerizing the polymerizable monomers.

20. The process according to claim 17, wherein the hydrophilic solid particles are selected from the group consisting of titanium oxide, silica, zeolite, barium sulfate, calcium carbonate, kaolin, and iron oxides.

21. The process according to claim 17, wherein the hydrophilic solid particles are comprised within the water droplets.

22. The process according to claim 17, wherein the hydrophilic solid particles are deposited on a surface of the water droplets.

23. A process for preparing an emulsion containing hydrophilic solid particles, comprising:

mixing a first water-in-oil emulsion with hydrophilic solid particles or a dispersion of lipophilic solid particles to form a mixture, wherein said first emulsion comprises water droplets; and sonicating the mixture with an ultrasonic dispersion device at an output of not less than 3 kW/m$^2$, to form a second water-in-oil emulsion containing hydrophilic solid particles;

wherein the hydrophilic solid particles are present in the second emulsion in an amount of not less than 40% by weight, based on the weight of the second emulsion; and wherein the water droplets contain the hydrophilic solid particles in the second emulsion.

24. The process according to claim 23, further comprising finely dividing the water droplets prior to and/or during the sonicating.

25. The process according to claim 23, wherein said water droplets comprise one or more polymerizable monomers; and wherein the process further comprises, after the formation of the second water-in-oil emulsion, polymerizing the polymerizable monomers.

26. The process according to claim 23, wherein the hydrophilic solid particles are selected from the group consisting of titanium oxide, silica, zeolite, barium sulfate, calcium carbonate, kaolin, and iron oxides.

27. The process according to claim 23, wherein the hydrophilic solid particles are comprised within the water droplets.

28. The process according to claim 23, wherein the hydrophilic solid particles are deposited on a surface of the water droplets.

* * * * *